United States Patent [19]

Lawrason

[11] 4,315,033

[45] Feb. 9, 1982

[54] METHOD OF TREATING MENOPAUSAL SYMPTOMS

[76] Inventor: F. Douglas Lawrason, 53 Spring Valley Rd., Convent Station, N.J. 07960

[21] Appl. No.: 227,354

[22] Filed: Jan. 22, 1981

[51] Int. Cl.³ .......................................... A61K 31/195
[52] U.S. Cl. ................................................... 424/319
[58] Field of Search ...................................... 424/319

[56] References Cited

PUBLICATIONS

E. S. Taylor, Essentials of Gynecology, Chapt. 33, 4th Ed. (1969).

Primary Examiner—Stanley J. Friedman

[57] ABSTRACT

This invention relates to a method of treating vasomotor instability, particularly in relation to the menopausal syndrome, by the administration of methyldopa.

6 Claims, No Drawings

METHOD OF TREATING MENOPAUSAL SYMPTOMS

BACKGROUND OF THE INVENTION

The term "menopausal syndrome" and its various symptoms have been well described in the literature (e.g. see Essentials of Gynecology, E. S. Taylor, Chapt. 33, 4th Ed., Publ. by Lea & Febiger, Phila., Pa. 1969). The usual symptoms consist of a variety of unpleasant and often highly distressing disturbances involving any or all of the systems of the body and result from hormonal imbalance, essentially from a deficiency of estrogens. Many different estrogens have thus been used in medicine for the treatment of menopausal syndrome.

Some symptoms mostly associated with the menopause are disturbances of the autonomic nervous system classified as vasomotor instability. Such symptoms of vasomotor instability in many patients are usually manifested in the form of excessive or inappropriate perspiration often accompanied by hot flashes (or hot flushes), tachycardia, nervousness, fatigue and insomnia and occasionally by irritability and other distressing secondary symptoms.

At present estrogen replacement therapy provides the most specific and effective method of treating the disturbing symptoms of menopause, including the aforementioned vasomotor symptoms. However, the many adverse and potentially dangerous side effects associated with the administration of estrogenic products are becoming increasingly apparent. For example, diethystilbestrol, a once widely used and well established estrogen, has been implicated as possibly being responsible for vaginal cancer and adenosis of the female offspring of pregnant women treated with the compound (Lancet 1975, 1960). Also ethinyl estradiol and mestranol, which represent estrogenic components in current oral contraceptives are now known to be involved in certain serious side effects associated with oral contraceptives including depression, (Nature 243,58 (1973)), hypertension (Am. J. Obstet. Gynecol. 112, 912 (1972)), carbohydrate and lipid abnormalities (Lancet 1969, Oct. 11, 783), interference with blood clotting mechanism resulting in thrombosis and stroke (Ann. Intern Med. 72, 111 (1970)), and jaundice (Am. J. Obstet. Gynecol. 119, 165 (1974)). Also, the administration of estrogens to postmenopausal women has been implicated as a cause of endometrial cancer (Science 191, 838 (1976)). Consequently, there is a need for an improved non-estrogenic method of treating those symptoms ascribed to vasomotor instability, particularly in relation to the menopausal syndrome.

DESCRIPTION OF THE INVENTION

This invention relates to a method of treating the symptoms associated with or resulting from vasomotor instability by the administration of methyldopa as the active ingredient. Methyldopa is the L-isomer of alpha-methyldopa, chemically identified as levo-3 (3,4-dihydroxyphenyl)-2-methylalanine. Its structural formula is:

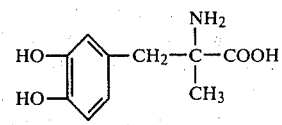

The widespread use of methyldopa as a uniquely safe and effective agent for treating hypertensive patients is so well documented in the scientific and medical literature and disciplines that very little need be further said here on this aspect of its utility. According to its recommended regiment for relieving hypertension, the usual starting dosage is 250 mg. two or three times a day in the first 48 hours followed by a maintenance daily dosage of 500 mg. to 2.0 g in two to four doses, the maximum recommended daily dosage being 3.0 g.

It has now been found that methyldopa effectively alleviates the symptoms of menopause, particularly those ascribed (supra) to vasomotor instability such as, for example, excessive perspiration, hot flashes, etc., upon systemic administration of at least 250 mg. per day, generally about 250 to 1500 mg. daily, and, preferably, about 500 to 1000 mg. daily, preferable in two to four doses. Within 48 to 72 hours such symptoms are markedly diminished in most patients and after four to five days complete or significant alleviation of symptoms is noted which continues as long as the medication is taken.

For therapeutic usage, the methyldopa is conveniently dispensed and administered in unit dosage form comprising 125–250 mg. in combination with a customary pharmaceutically acceptable carrier suitable for systemic administration, e.g. oral or parenteral. The commercial tablet forms presently available for treating hypertension which contain 125 and 250 mg. methyldopa are quite suitable although any of the customary solid or liquid pharmaceutical compositions made in accordance with conventional galenic pharmacy methods may be employed. Compositions in unit dosage form suitable for oral administration are preferred.

Since the proof of safety of methyldopa as a therapeutic agent has already been established, its usage for the purposes of this invention provides a welcome substitute for estrogen therapy by both patient and physician. There are no additional adverse effects to be concerned about except those already noted for methyldopa in its use in the treatment of hypertension.

In addition to being a safe agent for treating hypertensive individuals, it is also known that normal non-hypertensive individuals can be given methyldopa without any unusual or untoward effects. For the purposes intended herein, therefore, in the dosage recommended (supra) no significant drop in blood pressure is noted and thus no extraordinary pharmacological effects on the vascular system occur except for the desired beneficial effects on the underlying vasomotor disturbance or instability.

Accordingly, the instant invention provides a new spectrum of therapeutic utility for methyldopa, namely, the treatment of non-hypertensive patients manifesting symptoms of vasomotor instability. Primarily, such patients are females experiencing either natural menopause resulting from age-related declining ovarian function or premature or artificially induced menopause secondary to an ovariectomy, x-ray radiation etc. However, the symptoms of vasomotor instability are also experienced by both male and female patients not associated with menopausal disorders. Individuals manifesting such vasomotor instability are usually in the 20–45 year age range, in good health, non-hypertensive and with no underlying disease. However, during the normal course of the day they experience and exhibit excessive sweating over the entire body and particularly of the palms of the hands and the feet. They also often exhibit increased nervousness, occasional palpitation, fatigue and irritability. Methyldopa in the same dosage range (250–1500 mg. daily, 500–1000 mg. preferred) has been found to be effective in the treatment of the symptoms of these patients as well. The following example illustrates the use of methyldopa in effectively ameliorating vasomotor instability, as evidenced by excessive perspiration, in a male non-hypertensive patient.

EXAMPLE 1

Patient CM, a 27 year old male physician who was a medical resident in a major hospital, exhibited excessive and abnormal sweating much of every day even under cool environmental surroundings. His palms were constantly moist and he carried a towel with him at all times to wipe them. His feet were constantly wet and according to him he had consequently ruined three pairs of shoes in the previous two years and finally had settled on wearing athletic sneakers. His excessive perspiration was a persistent source of embarrassment especially during his contact with patients. Frequently the sweating was accompanied by tachycardia. A thorough diagnostic examination with laboratory tests was carried out and no organic cause for these symptoms of vasomotor instability was found. His blood pressure was normal. The patient was treated with 250 mg. methyldopa twice a day. Within 4–5 days most of his symptoms subsided. After one week of treatment the dose was increased to 750 mg. (250 mg. t.i.d.) with resultant complete disappearance of the symptoms while such dosage regimen was maintained. On four successive withdrawals of methyldopa, involving a month's control period without medication followed by a month on methyldopa (750 mg. daily), it was obvious that methyldopa was completely effective in controlling the vasomotor symptoms of this young man. No side-effects were observed.

The following six case histories illustrate the treatment with methyldopa of the distressing vasomotor symptoms experienced by non-hypertensive women during the menopause. All patients were followed for a period of time before starting methyldopa. This established a control period so the pattern and severity of symptoms could be assessed. The patients were then placed on methyldopa and followed for a period of from three to six weeks and the symptom pattern periodically evaluated and compared to the control period. The patients were then taken off methyldopa for a period of from one to four weeks and the baseline symptoms and signs were compared to the previous control and treatment periods. Some patients, because of the great relief experienced with methyldopa, objected to waiting four weeks without treatment, and thus were placed back on methyldopa in two to three weeks. All patients while receiving methyldopa experienced a significant alleviation of their symptoms and in some the symptoms were entirely suppressed, and thus they were essentially symptom-free. In others, the symptoms became barely discernible, were easily tolerated and considered no longer bothersome. The dosage was occasionally adjusted downward or upward depending upon the patient's response to the original prescribed dosage regimen and the severity of the symptoms until the methyldopa was able to effectively ameliorate the symptoms.

EXAMPLE 2

Patient EJ, a fifty-four year old female whose menses had stopped eighteen months before, had begun to experience drenching perspiration, hot flashes, and palpitation shortly thereafter. These occurred quite regularly at intervals of 20 to 30 minutes throughout the day and night. Her blood pressure was normal and she was in good health. Methyldopa was administered in a dosage of 250 mg. twice a day. By the second day the symptoms were less severe but had not disappeared. By the fourth day the patient was greatly relieved of her symptoms except for perspiration which, although much less, was still disconcerting. The dose of methyldopa was increased to 250 mg. three times a day and within forty-eight hours the excessive perspiration had disappeared.

She was continued on methyldopa (250 mg. t.i.d.) for a month and then treatment was discontinued. All symptoms returned by the third day. After two weeks of observation without medication, 250 mg. methyldopa t.i.d. was again begun with definite relief of symptoms beginning within the first twenty-four hours of treatment. By the third day while on 250 mg. t.i.d. all symptoms were suppressed to a level where they were no longer bothersome. The patient was taken off medication two more times after six weeks and two months treatment to assess the therapeutic impact of methyldopa. Each time the symptoms returned within three to five days, and were suppressed or disappeared once the patient was again placed on the methyldopa regimen.

EXAMPLE 3

Patient BR was a 47 year old non-hypertensive female who had been experiencing hot flashes, excessive perspiration, insomnia and tachycardia for four months. Her menses had been irregular for the preceding year. These symptoms were distressing enough to prompt her to seek help especially when she began to lose weight (about 15 pounds) and could not sleep because of her excessive nightly perspiration. After being given 500–750 mg. methyldopa a day for about one week, she was practically symptom-free and she began to sleep through the night. Within six weeks she had regained the weight lost since the onset of her menopausal symptoms. During the ten months the patient was under observation she was taken off methyldopa three times for periods of two to four weeks, and subsequently placed back on methyldopa (250 mg. t.i.d.) each time. Her symptoms promptly returned with each withdrawal of the drug, and effectively subsided with readministration.

EXAMPLE 4

Patient ET was a fifty-five year old female whose menses had stopped three years before. For these three years she had experienced the typical symptoms of the menopause and had been particularly bothered by tachycardia and palpitations which were accompanied by excessive sweating, hot flashes, etc. Her blood pressure was normal. During the periods of palpitation she would feel faint and dizzy and on two occasions she did lose consciousness for brief periods of time. She was placed on estrogen replacement therapy with some alleviation of her symptoms, but this was discontinued at the end of six weeks. She was then treated with 250 mg. methyldopa a day with moderate alleviation of symptoms. Since her palpitations and tachycardia began to recur about the third week, the dose was increased to 500 mg. a day (250 mg. b.i.d.). The tachycardia, sweating and hot flashes disappeared in a few days. This patient was then able to adjust her dosage regimen between 250 and 500 mg. a day depending upon the degree of concern she had over her symptoms and effectively maintain an essentially symptom-free state.

EXAMPLE 5

Patient KS was a forty-four year old non-hypertensive female who had experienced irregular menses for about fourteen months. For about ten months she noticed increasing symptoms of nervousness, irritability and overwhelming fatigue. These symptoms were accompanied by hot flushes, excessive sweating and palpitation. Because of these symptoms and particularly the signs of beginning depression, she was placed on estrogen replacement therapy. She then began to experience excessive bleeding during her menses and a D & C was performed. Excessive bleeding continued to occur and she was taken off estrogen therapy. For two months she was without therapy and her symptoms returned to greater degree of severity. Mental depression was evident and she was treated with amitriptyline, an antidepressant drug, with some, but not significant, improvement in her mental state. Her nervousness, irritability, fatigue and bouts of tachycardia continued. She was taken off amitriptyline and after two weeks was placed on 250 mg. methyldopa twice a day. Some amelioration of her symptoms occurred by the fifth day. One week later her dosage regimen was increased to 250 mg. three times a day and improvement continued. However, because of her palpitations and continued nervousness, the dose of methyldopa was increased to 250 mg. t.i.d. plus 250 mg. at bedtime. On this regimen improvement continued daily with complete cessation of her symptoms in about one week. Her mentally depressed state gradually disappeared and there was not longer any excessive bleeding. After three months she was taken off methyldopa completely, but was placed back on the 1000 mg. methyldopa regimen within two weeks because of the prompt return of the symptoms of the original frequency and severity, after which she was essentially symptom-free while the methyldopa regimen was maintained.

EXAMPLE 6

Patient PA at age 48 years had a hysterectomy because of fibroids. Her menses had been irregular for two years prior to her operation. About six months later she began to experience drenching night sweats, hot flushes and a tachycardia between 120 and 150 beats per minute. She had normal blood pressure. These symptoms were also present during the daytime, and would recur about every 30 minutes. Estrogen therapy was considered, but both physician and patient agreed that she should avoid estrogen replacement therapy because of her previous experience with uterine tumors. Methyldopa (250 mg. t.i.d.) was administered and within 3-5 days all her symptoms essentially disappeared. Only occasionally would she be aware that she had a mild warm or flushed feeling, but this was not bothersome. Her symptoms promptly returned at the same rate and severity upon discontinuation of methyldopa and subsided each time it was readministered.

EXAMPLE 7

Patient RK was a 45 year old fashion designer. She began to experience irregular menses and excessive perspiration and hot flashes, otherwise she was in good health. Her blood pressure was normal. Her excessive perspiration every half hour began to interfere with her career. Finally, methyldopa was tried 250 mg. twice a day with some improvement. After one week 250 mg. t.i.d. was given with a significant amelioration of the symptoms. Two weeks later she was given 250 mg. four times a day (q.i.d.) with complete cessation of the symptoms. On two subsequent occasions, methyldopa was discontinued with all symptoms previously experienced returning within one week. In each instance, 500-1000 mg. a day completely controlled her symptoms. She was thereafter able to adjust her own dosage regimen between 500 and 1000 mg. a day according to her best judgment for the control and effective amelioration of symptoms.

As described herein and as illustrated by the foregoing examples, the use of methyldopa to treat symptoms of vasomotor instability appears to be a remarkable and unexpected property in addition to its known antihypertensive activity. The perfect acceptability of the treatment, facilitated by the proven safety and general tolerance of methyldopa without any significant side effects and by its ease of systemic administration, particularly by the oral route, provides an excellent margin for its therapeutic success. Moreover, since methyldopa can be used without any fear of counter indications with respect to the danger of cancer, it provides an improved non-estrogenic method of treating menopausal related vasomotor symptoms.

In general, therefore, the instant invention provides a method of treating the symptoms of vasomotor instability in a non-hypertensive patient in need thereof which comprises systemically administering methyldopa to said patient in an amount sufficient to effectively ameliorate said symptoms, in general about 250-1500 mg. daily, and preferably about 500-1000 mg. daily, in divided doses. As a preferred embodiment, it provides a method of treating symptoms of vasomotor instability, particularly excessive perspiration, and/or hot flashes, associated with menopause in a non-hypertensive female in need thereof which comprises administering about 250-1500 mg. of methyldopa daily and 500-1000 mg. daily most preferred.

I claim:

1. A method of treating vasomotor symptoms associated with menopause in a non-hypertensive female in need thereof which comprises systemically administering methyldopa to said patient in an amount sufficient to effectively ameliorate said symptoms.

2. A method of treating vasomotor symptoms associated with menopause in a non-hypertensive female in need thereof which comprises systemically administering about 250-1500 mg. methyldopa daily to said patient.

3. A method of treating vasomotor symptoms associated with menopause in a non-hypertensive female in need thereof which comprises systemically administering about 500-1000 mg. methyldopa daily to said patient.

4. A method of treating excessive perspiration and hot flushes associated with menopause in a non-hypertensive female in need thereof which comprises systemically administering methyldopa to said patient in an amount sufficient to effectively ameliorate said symptoms.

5. A method of treating excessive perspiration and hot flushes associated with menopause in a non-hypertensive female in need thereof which comprises systemically administering about 250–1500 mg. methyldopa daily to said patient.

6. A method of treating excessive perspiration and hot flushes associated with menopause in a non-hypertensive female in need thereof which comprises systemically administering about 500–1000 mg. methyldopa daily to said patient.

* * * * *